United States Patent
Ebert et al.

(10) Patent No.: US 12,260,012 B2
(45) Date of Patent: Mar. 25, 2025

(54) METHOD AND SYSTEM FOR MONITORING A PERSON IN AN ENVIRONMENT

(71) Applicant: Siemens Healthineers AG, Forchheim (DE)

(72) Inventors: Anton Ebert, Schwaig bei Nuernberg (DE); Mathias Kraemer, Nuremberg (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 0 days.

(21) Appl. No.: 18/472,125

(22) Filed: Sep. 21, 2023

(65) Prior Publication Data
US 2024/0103609 A1    Mar. 28, 2024

(30) Foreign Application Priority Data
Sep. 22, 2022    (EP) ..................................... 22197113

(51) Int. Cl.
*G06F 3/01*    (2006.01)
*G02B 27/01*    (2006.01)

(52) U.S. Cl.
CPC ............ *G06F 3/011* (2013.01); *G02B 27/017* (2013.01); *G02B 2027/014* (2013.01); *G06F 2203/011* (2013.01)

(58) Field of Classification Search
CPC . G06F 3/011; G06F 2203/011; G02B 27/017; G02B 2027/014
See application file for complete search history.

(56) References Cited

U.S. PATENT DOCUMENTS

| 10,332,315 B2 | 6/2019 | Samec et al. |
| 2021/0043011 A1 | 2/2021 | Gates |
| 2021/0398357 A1* | 12/2021 | Samec ................. G02B 27/017 |

FOREIGN PATENT DOCUMENTS

KR    102355455 B1    1/2022

OTHER PUBLICATIONS

Barata P. et al.: "Consolidating Learning in Power Systems: Virtual Reality Applied to the Study of the Operation of Electric Power Transformers". In IEEE Trans. Educ. 58 (4), pp. 255-261. DOI: 10.1109/TE.2015.2393842.

(Continued)

*Primary Examiner* — Robert J Michaud
(74) *Attorney, Agent, or Firm* — Harness, Dickey & Pierce, P.L.C.

(57) ABSTRACT

One or more example embodiments of the present invention describes a method for monitoring a person in an environment, including integrating the person into the environment, wherein the person has a task to solve in the environment, measuring with a sensor system a number of physical conditions of the person while the person interacts with the environment, the sensor system providing a sensor-dataset including measured physical values about the person from which mental conditions of the person can be inferred, generating assessment-data from the sensor-dataset, the assessment-data reflecting at least one of an ability of the person to accomplish the task or the mental load of the person while solving the task, repeating the measuring and the generating a plurality of times and outputting the generated assessment-data or data based on the generated assessment-data.

20 Claims, 1 Drawing Sheet

(56) References Cited

OTHER PUBLICATIONS

Sharma N., et al., "Adaptive Learning in Medical Education: The Final Piece of Technology Enhanced Learning?", Ulster Med J. Sep. 2017;86(3):198-200. Epub Sep. 12, 2017. PMID:29581634; PMCID:PMC5849979.
"Adaptive Virtual Reality Training", in: https://avrt.training/ [abgerufen am: Aug. 30, 2023].
Tobii Connect "How do Tobii eye trackers work?", reflections (https://www.tobiipro.com/learn-and-support/learn/eye-tracking-essentials/how-do-tobii-eye-trackers-work/), Screenshot Nov. 18, 2022.
LRQA "Adaptive eLearning—Eine Trainingsmethode für zielgenaue Lernerfolge". https://www.lrqa.com/de-de/news/adaptive-elearning/.
Schultheiss O. et al."Implicit Motives", Handbook of Personality: Theory and Research (4 ed., pp. 385-410). New York: Guilford.
Seel N. et al.: "Encyclopedia of the Sciences of Learning". Boston, MA: Springer US (Springer reference)., ISBN 978-1-4419-1427-9, 2011.
Cook D. et al.: (2008): Internet-based learning in the health professions: a meta-analysis. In JAMA 300 (10), pp. 1181-1196. DOI: 10.1001/jama.300.10.1181.
Kröger, J.L., et al. (2020). What Does Your Gaze Reveal About You? On the Privacy Implications of Eye Tracking. In: Friedewald, M., Önen, M., Lievens, E., Krenn, S., Fricker, S. (eds) Privacy and Identity Management. Data for Better Living: AI and Privacy. Privacy and Identity 2019. IFIP Advances in Information and Communication Technology(), vol. 576. Springer, Cham. https://doi.org/10.1007/978-3-030-42504-3_15.
Krol LR. et al.: "Neuroadaptive Technology: Concepts, Tools, and Validations". Dissertation. Technischen Universität Berlin, Berling. Fakultaet V—Verkehrs- und Maschinensysteme, checked on May 19, 2022.
Scientific studies: e.g., Multi-Kohorten-Sequenz-Designs (https://dorsch.hogrefe.com/stichwort/multi-kohorten-sequenz-designs).
Siegel E.H et al. (2021): "HP Omnicept Cognitive Load Database (HPO-CLD). Developing a Multimodal Inference Engine for Detecting Real-time Mental Workload in VR". HP Labs. Palo Alto. Available online at https://developers.hp.com/system/files/attachments/HPO-CLD%20Technical%20Report%204.30.21.pdf, checked on Jan. 27, 2022.
Miller E.K. et al.: "An integrative theory of prefrontal cortex function. In Annual review of neuroscience" 24, pp. 167-202. DOI: 10.1146/annurev.neuro.24.1.167.
"Cognitive Load Open Dataset", HP Developers Portal: https://developers.hp.com/omnicept/read-me-cognitive-load-open-dataset?language=de.
Wood, David, et al. "The role of tutoring in problem solving." Journal of child psychology and psychiatry 17.2 (1976): 89-100.
"Skilitics Health", in: https://www.skilitics-health.com/solutions/radiography [abgerufen am Aug. 30, 2023].
"Fitbit", "Track, unpck and manage a stress" https://www.fitbit.com/global/us/technology/stress#:~:text=Meet%20the%20world's%20first%20EDA,your%20body's%20response%20to%20stress).
HP developers "Fundamentals", engine. https://developers.hp.com/omnicept/docs/fundamentals.
"Adaptive Training", in: https://www.trainerroad.com/adaptive-training [abgerufen am Aug. 30, 2023].
Sweller, John. "Cognitive load theory." Psychology of learning and motivation. vol. 55. Academic Press, 2011. 37-76.
Chiossi F. et al.: "Virtual Reality Adaptation Using Electrodermal Activity to Support the User Experience". In BDCC 6 (2), p. 55. DOI: 10.3390/bdcc6020055.
Mishra J. et al.: "Video Games for Neuro-Cognitive Optimization". In Neuron 90 (2), pp. 214-218. DOI: 10.1016/j.neuron.2016.04.010.
"Elsevier Adaptive Quizzing (EAQ)", in: https://evolve.elsevier.com/education/eaq/ [abgerufen am Aug. 30, 2023].
Bossard C. et al.: "Transfer of learning in virtual environments: a new challenge?" In Virtual Reality 12 (3), pp. 151-161. DOI: 10.1007/s10055-008-0093-y.
Anguera J., et al.: "Video game training enhances cognitive control in older adults", Nature. Sep. 5, 2013; 501(7465): 97-101. doi:10.1038/nature12486.
Mishra, J., et al.: "Harnessing the neuroplastic potential of the human brain & the future of cognitive rehabilitation", Front. Hum. Neurosci., Apr. 11, 2014 Sec. Brain Imaging and Stimulation vol. 8—2014 | https://doi.org/10.3389/fnhum.2014.00218.

* cited by examiner

METHOD AND SYSTEM FOR MONITORING A PERSON IN AN ENVIRONMENT

CROSS-REFERENCE TO RELATED APPLICATION(S)

The present application claims priority under 35 U.S.C. § 119 to European Patent Application No. 22197113.8, filed Sep. 22, 2022, the entire contents of which are incorporated herein by reference.

FIELD

One or more example embodiments of the present invention pertains to a method and a system for monitoring a person in an environment in order to enhance the solution of tasks in this environment. In addition, one or more example embodiments of the present invention connects cognitive load and biometric sensor data to improve a learning experience or the execution of work.

RELATED ART

Digital applications or virtual environments are up to now not able to adaptively change their user interface and other visual or structural elements, e.g. quantity and type of user guidance or informational content, in real-time and without intentional user participation. Application can only cater to the average user and not the individual, e.g. different types of users that absorb and process information differently or even users being in a different mood at different times. Consequentially they are not as effective as they could be, especially compared with a similar case comprising a communication with real humans.

Looking at the digital education sector, there is existing software that is set out to be "adaptive", however, it only changes ad hoc after an active user interaction, e.g. based on bad test results in the application according to a scoring system result in changes in future iterations of the learning content.

An exemplary training software uses an 'adaptive self-assessment module', which is a quiz that users can solve after a VR simulation of an x-ray procedure (VR: virtual reality). The topics covered in the quiz concentrate on particular aspects which were incorrectly or inaccurately executed in the preceding VR simulation. In this case the results of procedure steps (that are invisible to the user) are the decisive factor for the composition of the subsequent quiz. However, they don't change the VR experience in real-time, but only based on the quiz.

Another example is an "adaptive" learning platform that is used to assist health science users, by predicting performance per user to determine what they already know and what they need to know, helping to ensure an understanding of higher level tasks. Here, again, a user solves a quiz, wherein future questions in the quiz are influenced in regard to the results of the previous questions.

A "teach-by-asking" concept checks individual users' level of knowledge. Here, also, a quiz is solved, wherein the answers can be given with a percentual certainty and an algorithmic analysis of the answers compiles the training based on this data.

There is also an adaptive training for workout (e.g. cycling or spinning), wherein different training levels are based on individual progression levels which represent the fitness level of a user and incorporates results from former training.

In military training, there is an "adaptive" approach, wherein an experienced instructor designs the training based on different building blocks. Integrated real-world weapons and objects, detailed environments and an extensive library of characters, weapons and situations allow the instructor to build a training simulation that's tailored to the exact learning outcomes desired, delivering existing curricula and frameworks.

SUMMARY

The drawback of all these concepts is that adaptiveness is only possible after a willful action of the user or a trainer. Real-time adaptiveness cannot be achieved and the system could be misled by misleading actions. For example, may a user luckily guess the right answers of a quiz and be confronted afterwards with a further, "adapted" quiz that seriously exceeds the knowledge of the user.

Example embodiments improve on the known systems, devices and methods to facilitate an improvement in monitoring a person in an environment and especially control or rate an environment based on the monitoring results.

BRIEF DESCRIPTION OF THE DRAWINGS

Features of example embodiments will become apparent from the following detailed descriptions considered in conjunction with the accompanying drawings. It is to be understood, however, that the drawings are designed solely for the purposes of illustration and not as a definition of the limits of the invention.

In the diagrams, like numbers refer to like objects throughout. Objects in the diagrams are not necessarily drawn to scale.

DETAILED DESCRIPTION

Figure 1:
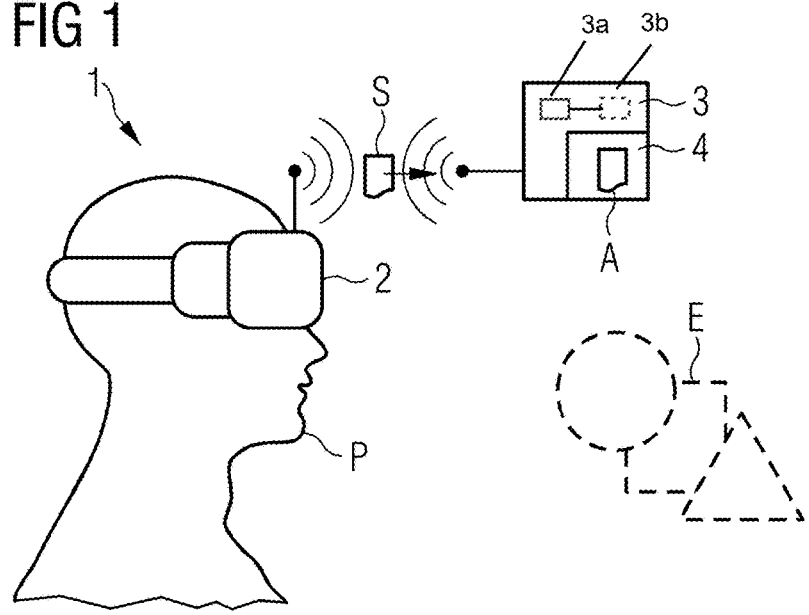
FIG. 1 outlines an example for a setup of the system according to one or more example embodiments of the present invention.

A method according to one or more example embodiments of the present invention is adapted for monitoring a person in an environment. Actually, it does, at first hand, not matter what environment is used. It could be a (real) work environment, e.g. an assembly hall, or a classroom. However, one or more example embodiments of the present invention is especially advantageous for virtual environments (in virtual reality) or a real environment with virtual supplements (augmented reality). An environment could also be a test, where questions have to be answered or a learning environment, where content to be learned is provided. The user is a person to be assessed or a person having a task to solve, e.g. finishing a work or solving a test or learning a unit.

For example, a learning environment should be adapted in that additional information is provided explaining certain aspects of the unit, wherein the content of the additional information depends on the load factor of the user. Another example is an augmented working environment, wherein, depending on the work progress of the person, additional information is provided helping to finish the work. In a third example, the complexity of a game is adapted to the skills of a user.

A method comprises the following steps:
a) integrating the person into the environment, wherein the person has a task to solve in the environment,
b) measuring with a sensor system a number of physical conditions of the person, while the person interacts with the environment and wherein the sensor system provides a sensor-dataset comprising measured physical values about the person, from which mental conditions of the person can be inferred,
c) generating assessment-data from the sensor-dataset, wherein the assessment-data reflects the ability of the person to accomplish the task and/or the mental load of the person while solving the task,
d) repeating steps b) and c) a plurality of times,
e) outputting the generated assessment-data or data based on the generated assessment-data.

At first, the parson has to be integrated into the environment. That could easily happen by entering a room or entering a virtual reality, where the task has to be solved. Even books or papers could be a possible environment in the case, the person has to learn something. Also taking seat in front of a computer screen could be an integration of the person.

The task could be anything the person has to do in the environment. A task could be: doing work, solving a level in a game, learning content, reaching a goal of an exercise, or physical or mental training. Even to take part in a military simulation could be a task.

While the person interacts with the environment, i.e. trying to solve the task, e.g. learning, working training, finishing a quiz, physical conditions of the person are measured with the sensor system. It should be noted that there is not measured arbitrary physical data (e.g. size or weight), but physical values about the person, from which mental conditions of the person can be inferred (e.g. blood pressure, brain activity, oxygen uptake, head temperature, skin resistance, etc.). It is preferred that the sensor data is obtained by measuring physical parameters of the person that are depending from the autonomic nervous system of the person. Signals of the autonomic nervous system are, generally, involuntary and are, therefore, reflecting the condition of the person in an objective way. By using this autonomic nervous system, data can be processed that the person did not intend to use for communication or control and the person isn't even aware of. This data can give information about inner workings/states of mind of the person, without any active involvement of the person. Therefore, they could be processed in real-time and open novel human-computer interaction paradigms.

With this sensor data, the "assessment-data" is generated. This is a generic expression and pertains to the ability of the person to solve the task or the load of the person while solving the task. The assessment-data reflects in a quantitative manner the ability of the person to accomplish the task and/or the mental load of the person while solving the task. This means that this assessment-data is a quantitative value or an array of values (especially a list of values over a certain time). The assessment-data could comprise or even be the "cognitive load", a commonly used quantitative value of the load of a person in the state of the art.

For example, the brain activity of a person could be measured while learning a unit or while solving a quiz. This brain activity could be computed to one value, e.g. by adding up the measured activity data of the brain, especially normalized, over the time of learning or solving the quiz. The absolute values of the assessment-data, compared to other persons or a reference, or a fluctuation of values of the assessment-data over time could give a first impression of the load of the person while learning or solving the quiz.

The assessment-data is preferably designed such that it reflects the ability of the person to solve the task and/or that it reflects a mental load of the person while solving the task, e.g. said cognitive load CL. The cognitive load indicates how mentally busy the person is at a certain point in time. This does not mean that a very high or low value is good. Rather a medium value is preferred showing that the person thinks, but is not exhausted or overburdened. The value for Cognitive Load is based on the theory of the same name: Cognitive Load Theory (CLT) introduced first by Sweller in 1988. According to CLT, a medium CL value would describe a state of mind in which users would be able to learn, because they are mentally neither overwhelmed nor under-challenged from the task at hand. A medium CL value would theoretically be a value of ~0.5 when looking at the full CL value scale from 0.0 to 1.0, but in reality, probably varying in regards to minimum, maximum and mean because of the individual capacity of the users. The wording "would be able to learn" is intentional because, this data alone would not be sufficient to prove learning success. Supposing the learning content and design would be ideal, the user would have been in a state of mind in which learning could have occurred. Learning success would always require a result in the form of e.g., a score in an exam, quiz, or test or even better in a longitudinal analysis of students trained with the system in the workplace and measuring the positive effect on the patient outcome in the field in a study that examines learning retention.

The above steps are repeated a plurality of times to get a plurality of values for the assessment-data, especially a progression of values over time.

Last, the generated assessment-data is outputted. However, since sometimes a user may not want to work with raw data, a rating "poor", "medium", "good" could be outputted, instead. Also control data based on the assessment-data could be outputted instead, e.g. "output additional hint", "output additional excessive help", "simplify quiz". These are examples for data based on the generated assessment-data. For example, the certain value of the assessment-data could be displayed in virtual or augmented reality like a fitness tracker or a number floating in space.

In fact, a serious benefit of one or more example embodiments of the present invention could be gained, if the assessment data is used not (only) to inform a user, but used to amend or adapt the environment. For example, the complexity of the task, of content accompanying the task or of the environment could be adapted to the assessment-data or additional information could be displayed.

For example, the person should learn a unit. During a certain step, the assessment-data fluctuates (since the person had not understood a certain item of the content and loses track). Using the method, the assessment data could be examined for fluctuations and automatically additional content (e.g. explanations to items of the certain step) could be displayed, when fluctuations occur.

Regarding a game, resistance of the skin could be measured for generating assessment data. If the assessment data shows increasing transpiration, the speed of the game or the number of virtual combatants could be reduced (e.g. in the first levels where a feeling of success should be provided).

As third example, in virtual reality a job should be processed, e.g. a programming, operating or designing job.

The headset (head up display, HUD) of the user comprises a wide variety of sensors, including a sensor for eye activity. This sensor could then be used to generate assessment data comprising or being the cognitive load CL of the person. Then, depending on the CL or fluctuations of the CL, complexity of the virtual environment could be adapted. For example, for a programming or designing job, the number of visible "tools" could be adjusted or during a (medical) operation, additional information could be visualized or hidden.

A system according to one or more example embodiments of the present invention for monitoring a person in an environment, is designed to perform a method according to one or more example embodiments of the present invention. This system comprises the following components:
- a sensor system designed to measure the physical condition of the person while interacting with the environment and for providing a sensor-dataset comprising the measured values,
- a generation unit designed for generating an assessment-data from the sensor-dataset,
- an output interface designed for outputting the generated assessment-data or data based on the generated assessment-data.

The function of these components has already been explained above. The system can be used in any educational and service application and will enhance the application in a way that individuals can consume better targeted education or services which again is a value add to any application and results in additional revenue potential and cost savings in the internal as well as external environment.

In addition to the state of the art, where user data is only extracted and evaluated ad hoc, even if it is accumulated in real-time, the user data (i.e. the assessment-data) of the preset invention could be fed back into a control system of the task or of the environment. This data could not only be displayed to the users to inform them with the aim to raise self-awareness, but also automatically be processed in the background to influence the users' surroundings to their advantage. The advantage is an application that can on a high-level, adapt to different users and their learning or information processing style and on a low-level, adapt to the same user differently based on their daily emotional or cognitive condition.

An example for this could be a training software, which increases guidance (in this context: scaffolding) for inexperienced users that are overwhelmed by the educational content or even the virtual environment per se, through additional displayed information. The more experienced the users is the less scaffolding could be deployed, leading to a more self-determined and efficient learning experience in a simulation, which has shown to be more effective than a guided training.

Some units or modules of the system mentioned above can be completely or partially realized as software modules running on a processor of a respective computing system, e.g. a VR system. A realization largely in the form of software modules can have the advantage that applications already installed on an existing computing system can be updated, with relatively little effort, to install and run these units of the present application. An object of one or more example embodiments of the present invention is also achieved by a computer program product with a computer program that is directly loadable into the memory of a computing system, and which comprises program units to perform the steps of the inventive method, at least those steps that could be executed by a computer, especially steps b) to e), when the program is executed by the computing system. In addition to the computer program, such a computer program product can also comprise further parts such as documentation and/or additional components, also hardware components such as a hardware key (dongle etc.) to facilitate access to the software.

A computer readable medium such as a memory stick, a hard-disk or other transportable or permanently-installed carrier can serve to transport and/or to store the executable parts of the computer program product so that these can be read from a processor unit of a computing system. A processor unit can comprise one or more microprocessors or their equivalents.

Particularly advantageous embodiments and features of one or more example embodiments of the present invention are given by the dependent claims, as revealed in the following description. Features of different claim categories may be combined as appropriate to give further embodiments not described herein.

According to a preferred method, the environment is an at least partially simulated environment, especially a virtual reality (VR) or an augmented reality (AR). In virtual reality, the person typically wears a headset with two displays in front of the eyes that show the virtual environment. In augmented reality, the person is in a real environment that is enhanced with digital content (digital objects) shown on a display, especially of a headset or glasses. However, there are other virtual environments possible, incorporating varying degrees of real-world elements, from fully digital VR to mostly real AR?

Preferably, at least one of the sensors of the sensor system is a sensor of a headset (a HUD used to create a virtual reality or an augmented reality). Other preferred sensors are described below. However, it is not necessary that the sensors must be always in the headset. There only must be a simultaneous measurement of the sensors while the person solves the task, especially in VR or AR.

According to a preferred method, the assessment-data comprises a quantitative value of the attention and/or concentration and/or alertness of the person, especially a cognitive load value (or comprises a proceeding amount of CL values in time). It is preferred that the assessment-data reflects a quantization of
- emotions, especially valence and/or arousal and/or being in a flow state (e.g. excited, astonished, delighted, happy, pleased, content, serene, calm, relaxed, sleepy, tired, bored, depressed, miserable, frustrated, annoyed, angry, afraid, alarmed, angry),
- change of emotions (e.g. a change of above listed emotions),
- relation of the person to an actual task (e.g. being concentrated, relaxed, attentive, motivated or distracted, stressed, inattentive, unmotivated),
- the person being mentally capable of doing the actual task (e.g. by a rating score or the time the solving of the task takes),
- the person being physically capable of doing the task or knowing how to do the task,
- how the person experiences the task,
- physical discomfort of the person (e.g., measuring cyber sickness in VR, i.e. a state where hardware issues (for example bad framerate) stand in the way of a good VR experience because the user is feeling nauseated),
- immersion and presence in virtual reality or augmented reality,
- intelligence of the person, implicit motives (i.e. Schultheiss's implicit motives: Implicit motives are motivational dispositions that operate outside of a person's conscious awareness and are aimed at the attainment of specific classes of incentives and the avoidance of specific classes of disincentives).

According to a preferred method, based on a plurality of assessment-data generated while repeating steps b) and c), a trend is calculated. With "trend", preferably the first derivative respective to time of the assessment-data being a progression of values in time, is meant or an evaluation of this first derivative. When repeating steps b) and c), there are multiple assessment-values collected, forming in their sum the assessment data. These assessment values could be plotted as a graph against time, or processed by calculating the slope of the graph (i.e. the first derivative respective to time). There could be an upward, downward or constant trend. Also, fluctuations could be monitored, especially with the first derivative crossing the Zero-line. Also the second derivative respective to time could be calculated.

It is preferred that an average of the assessment-data over a specific time frame is calculated, e.g. the last 10 seconds, and the last assessment-data is compared with the average or a gradient respective to time of the progression of the assessment-data is calculated. Thus, the average could be used as a threshold or for a rating. Concerning a rating of the person or of the situation, preferably a classification of discrete levels of assessment-data is adapted to the person, e.g. "low", "medium" and "high") based on minimum, maximum and average assessment-data. However, looking at the CL, where a medium value is best, the rating of the assessment-data (especially of an average) could also be based on the diversion of a central value.

In real applications, a baseline could be procured at the beginning of each person test when the person is already monitored by the sensor system (e.g. wearing a headset) but not exposed to any stimulus or task yet. This would additionally rule out that the sensor system alone is increasing CL, because the person has no experience with the environment (e.g. with VR). The value for the average and the maximum should be identified as the test progresses and more data for the specific person is gathered. Heuristically set proxy values could be used in the beginning when there is little or no data from the person and be replaced gradually as the test progresses with a value that is more realistic based on the gathered data, these models could also be potentially saved for each person, which increases its adaption speed the next time they use it and it could also be used to infer more information by comparing minima, maxima and averages (meant is the assessment-data) of different days of the person. As an alternative for calculating an average it could be practical to calculate the differential quotation of the values of a time series or a (e.g. linear) regression analysis, to indicate the algebraic signs of the gradients and therefore identify and upwards or downwards trend.

According to a preferred method, the generated assessment-data is used for controlling a system biasing the environment. As already said above, this is a very advantageous point of one or more example embodiments of the present invention. The environment could not only be amended ad hoc, but right after the assessment-data is generated and analyzed, e.g. by recognizing trends, fluctuations or aberrations from the "good" center. The following examples could by applied one for one or in combination.

It is preferred that the system outputs a warning in the case the cognitive load value is outside a predefined range. This warning could range from an "aggressive" way, to just creating a general awareness for the assessment-data (e.g. CL) to the user. The former would act more as a prompt, the latter could help the user link these positive or negative states of mind to their own actions, teaching them to percept them more voluntarily.

It is preferred that the system provides learning content and the complexity of the learning content and/or additional information is controlled depending on the assessment-data. This "control" could be a reduction or enhancement of complexity depending on the assessment-data or providing additional help or explanations. Especially, based on the assessment-data, learning content can be varied in regard to: different topics, extent of information, complexity of content, variety (way of encoding of information, e.g. visual, such as images or video), auditive or haptic).

It is preferred that complexity of a virtual environment is reduced or enhanced depending on the assessment-data. Since virtual rooms could have a very complex texture and many objects (not necessarily belonging to the task), such items could be reduced or enhanced. For example, a person that is fully occupied by the task of a game does not need complex textures, wherein a person able to solve the task easily sometimes want to feel into the atmosphere of the virtual reality. This aspect is especially advantageous for games in virtual reality. Thus, complexity of the environment can be adapted to a user so that concentration, e.g. on learning content, could be enhanced.

It is preferred that complexity of the task is reduced or enhanced depending on the assessment-data. Especially at the beginning of a series of tasks, it is advantageous to provide persons solving the task a feeling of confirmation of their abilities. Thus, tasks at the beginning of such series could be tailored to the abilities of the person.

It is also preferred that substances enhancing the condition of the person are provided. This could be food, drinks or medication.

As said above, it is not necessary to output the assessment-data directly, but also data based on the assessment data, such as a rating or control data. Thus, according to a preferred method, data based on the generated assessment-data is control data designed to control a device that changes aspects of the environment, preferably visible, audible or haptic aspects or content provided in the environment. This could e.g. be additional information for learning, a number of sub-tasks to solve or complexity of the environment and/or a user interface (see above). Such data could especially be "multimodal" data, such as visual, auditory, somatosensory, olfactory or gustatory data.

According to a preferred method, visual and/or auditive and/or olfactory and/or haptic and/or somatosensory and/or gustatory aspects of the environment are changed based on a number of the generated assessment-data. The change is especially based on the latest part of generated assessment-data or trends of the assessment data, preferably wherein this change comprises the change of the following aspects:

- the intensity and/or color of a light source of the environment, e.g. the lighting of the scene (ambient light, "sun"), gently changes in brightness or color depending on a CL value,
- information on a head up display, watch or display-wristband,
- the appearance of objects placed in a virtual or augmented environment,
- a vibrotactile feedback, especially the change of a specific vibration pattern through a feedback device, e.g. of a haptic glove, an auditive feedback, especially by triggering a buzzing, a melody or an alarm, a virtual information object in a virtual environment or an augmented reality or in a user interface, especially an individual information label.

Besides generating assessment-data for a single person, is also preferred to generate one single set of assessment data of a group of persons. However, since the individuals of a group may offer more information than the group itself, it is also advantageous to have data of each individual person.

According to a preferred method, two or more persons are monitored in the environment by measuring with the sensor system a number of physical conditions of each person, while the persons interact with the environment. Thus, there are individual sets of assessment-data of the persons. It is preferred that the assessment-data generated from the sensor-dataset is generated for each person and reflects the ability of the respective person to accomplish the task, and/or is generated for the group of persons and reflects the ability of the group to accomplish the task, and/or is used for a rating of the environment by comparing the assessment-data of the persons with a predefined value and/or classifying the load values of the persons and/or comparing the assessment-data of the persons with assessment-data of persons of another environment, and/or is used for further developing the environment and/or is used for assessing or classifying the persons.

If e.g. cognitive load is used in a context to give information about the application's or the person's quality or abilities in a multi-user scenario a novel approach could be not to only grade each person individually but to rate a whole group in the case when this group is undertaking one task together. A joint cognitive load measurement for the whole group could be more robust and in accordance with the truth than individual CL measurements. Because in a group setting more experienced person could help out low experienced ones, but the CL measurements of these persons of high and low level would need to be balanced in regard to the overall Group-CL calculation According to a preferred method, the environment provides a simulation, a learning procedure, a training procedure or a game. It is then preferred that the course of the content of the environment is changed depending on the assessment-data. This means that there are multiple possible courses that could maybe be present as fixed possibilities in a memory or could be prepared dynamically. What course is chosen next (e.g. the difficult one or the easy one) depends on the assessment-data. It should be noted that "next" does not necessarily mean "after a sub-topic is solved", but could also mean "for the next step" or "in the next second".

It is preferred that the environment comprises adaptive scaffolding properties, wherein the adaptive scaffolding is designed to comprise several grades of scaffolding, wherein depending on the assessment-data the grade of scaffolding is selected and provided to the person in the environment. Alternatively or additionally it is preferred that the environment comprises different levels of difficulty, wherein depending on the assessment-data a level of difficulty is selected and provided to the person in the environment. Alternatively or additionally it is preferred that the environment comprises means to interrupt a proceeding on the environment or display an alert, wherein depending on the assessment-data the proceeding is interrupted or an alert signal is provided to the environment (e.g. a "hand rise" is triggered in a video conference).

According to a preferred system, the generation unit is designed to additionally generate data based on the generated assessment-data, especially alarm-data, feedback-information, classification data of persons, rating data of the environment or control-data.

According to a preferred system, the generation unit comprises a machine learning model trained on a multitude of sensor-datasets, each sensor-dataset being labeled with detected assessment-data.

According to a preferred system, the sensor system comprises a number of sensors of the group containing:

eye tracking sensors, wherein the physical condition comprises eye movement and/or eye opening and closure (e.g. blink duration or frequency, distance between eyelids) and/or eye status (e.g. reddened, dry, watery) and/or pupil properties (e.g. pupil dilatation, reactivity, size) of the person, photoplethysmogram sensors, wherein the physical condition comprises blood volume changes, especially in the microvascular bed of tissue, accelerometers and/or Gyroscopes, wherein the physical condition comprises movements and/or inclination, electrocardiogram (ECG) sensors, wherein the physical condition comprises heartbeat, photoplethysmogram (PPG) sensors, wherein the physical condition comprises heartbeat and/or breathing, electro-encephalograph (EEG) sensors, wherein the physical condition comprises brain activity, electromyography (EMG) sensors, wherein the physical condition comprises muscle movements, electrodermal activity (EDA) sensors, wherein the physical condition comprises perspiration, visual sensors, especially cameras, wherein the physical condition comprises eye condition and/or movements of the person and/or posture of the person, glucose sensors, wherein the physical condition comprises blood sugar condition, temperature sensors, wherein the physical condition comprises body temperature, humidity sensors, wherein the physical condition comprises perspiration, blood pressure sensors, wherein the physical condition comprises blood pressure, blood oxygen saturation monitoring sensors, wherein the physical condition comprises blood oxygen, auditory sensors, wherein the physical condition comprises a voice of the person.

Especially eye tracking sensors, photoplethysmogram sensors and accelerometers and/or Gyroscopes could be integrated in a headset for virtual or augmented reality.

In a preferred system according to one or more example embodiments of the present invention, components of the system, especially the generation unit, are part of a data-network, wherein preferably the data-network and the sensor system are in data-communication with each other, wherein the data-network preferably comprises parts of the internet and/or a cloud-based computing system, wherein preferably the generation unit of the system is realized in this cloud-based computing system. For example, the components of the system are part of a data-network, wherein preferably the data-network and a medical imaging system which provides the image data are in communication with each other. Such a networked solution could be implemented via an internet platform and/or in a cloud-based computing system.

The method may also include elements of "cloud computing". In the technical field of "cloud computing", an IT infrastructure is provided over a data-network, e.g. a storage space or processing power and/or application software. The communication between the user and the "cloud" is achieved via data interfaces and/or data transmission protocols.

In the context of "cloud computing", in a preferred embodiment of the method according to the invention, provision of data via a data channel (for example a data-network) to a "cloud" takes place. This "cloud" includes a (remote) computing system, e.g. a computer cluster that typically does not include the user's local machine.

Within the scope of a preferred embodiment of the system according to the invention, the abovementioned units (especially the generation unit) are present on the "cloud" side. A preferred system further comprises, a local computing unit connected to the system via a data channel (e.g. a data-network, particularly configured as RIS or PACS). The local computing unit includes at least one data receiving interface to receive data. Moreover, it is preferred if the local computer additionally has a transmission interface in order to send data to the system.

FIG. 1 outlines an example for a setup of the system 1 for monitoring a person P in an environment E. A person P wears a headset 2 (a HUD) that provides the impression of a virtual reality to this person and additionally acts as sensor system 2. There are some objects drawn with dashed lines symbolizing the (virtual) environment E provided to the person P. It should be noted that actually the whole graphical "world" the person can see through the monitors of the headset could be counted as environment E. The system 1 is designed to perform a method outlined in the following figures.

The system 1 comprises said sensor system 2 of the headset 2 that is designed to measure the physical condition of the person P while interacting with the environment E. The sensor system 2 (headset 2) may comprise an eye tracking sensor inside its head-mounted display that captures eye movement and pupil dilation, e.g. by using a technique called pupil center corneal reflection, where a light source illuminates the eye and a camera is used to capture the resulting visible reflections. The part of the sensor-dataset S measured with this eye tracking sensor may be: gaze, pupil position, pupil dilation and eye openness. Additionally, a photoplethysmogram sensor may be included that detects the blood volume changes in the microvascular bed of tissue using light signals that reflect onto the skin. The PPG sensor could be located on the forehead, represented by two green LEDs. The part of the sensor-dataset S measured with this PPG may be the heart rate, wherein the heart rate variability may be derived from measured heart rate values.

The sensor-dataset S is then sent (via wireless communication indicated by the antennae) to a generation unit 3 that generates assessment-data A from the sensor-dataset S. In some example embodiments, this may be achieved by processing circuitry 3a on the generation unit 3 (e.g., a microprocessor) that executes a programmed algorithm or by a machine learning model trained on a multitude of sensor-datasets S stored in within the processing circuitry or a memory 3b.

The generated assessment-data is then outputted by the output interface 4. It could be used to inform the person P about the cognitive load during the solution of a task in the environment or to ament the environment.

Figure 2:
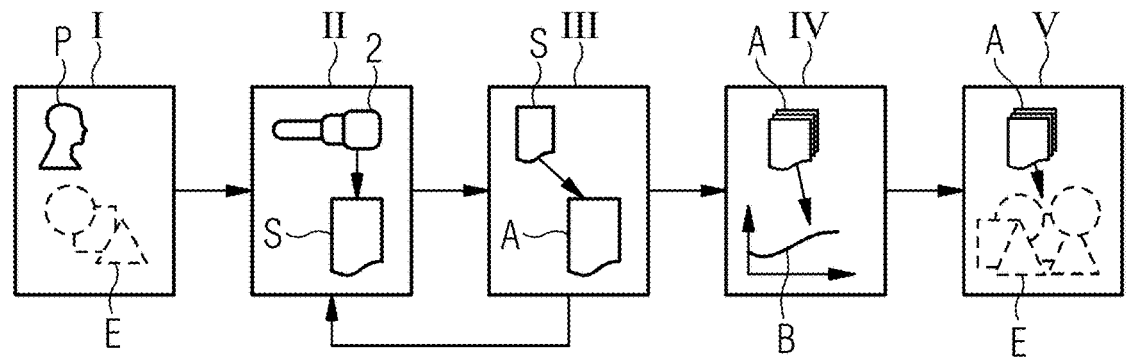
FIG. 2 shows a block diagram for the execution of a preferred method according to one or more example embodiments.

FIG. 2 shows a block diagram for the execution of a preferred method for monitoring a person P in an environment E (see e.g. FIG. 1).

In step I, the person P is integrated into the environment E and has a task to solve in the environment E, e.g. learning, solving a level of a game or working. The integration into the environment could be realized by putting on a headset and starting a VR-scenario. Shown are here some objects in dashed lines representing a virtual environment.

In step II the sensor system 2 of the headset measures a number of physical conditions of the person P, while the person P interacts with the environment E (e.g. learns a lesson, playing a game, working) and wherein the sensor system 2 provides a sensor-dataset S comprising measured physical values about the person P (see e.g. the above description to FIG. 1). It is important that mental conditions of the person P can be inferred from the sensor dataset S, since the assessment-data A should reflect these mental conditions.

In step III, the assessment-data A is generated from the sensor-dataset S, wherein the assessment-data A reflects the ability of the person P to accomplish the task (e.g. solving the level of the game or finishing the work) and/or the mental load of the person P while solving the task (e.g. during learning).

The arrow back to step II indicates that steps II and III are repeated a plurality of times.

In step IV, a progression B of assessment-data A is generated from the generated assessment data A over a time period and a trend is observed. Here the trend is rising what is in the case of this example a good sign. In an example, where cognitive load is generated as assessment-data A, an optimum would be when the CL-value would right be "in the middle".

In step V, the generated assessment-data A is used to amend the environment E. The addition of new objects compared to step I should indicate that the complexity of the environment E is enhanced (e.g. the complexity of the game, the graphical resolution is enhanced or the learning content is more challenging).

Figure 3:
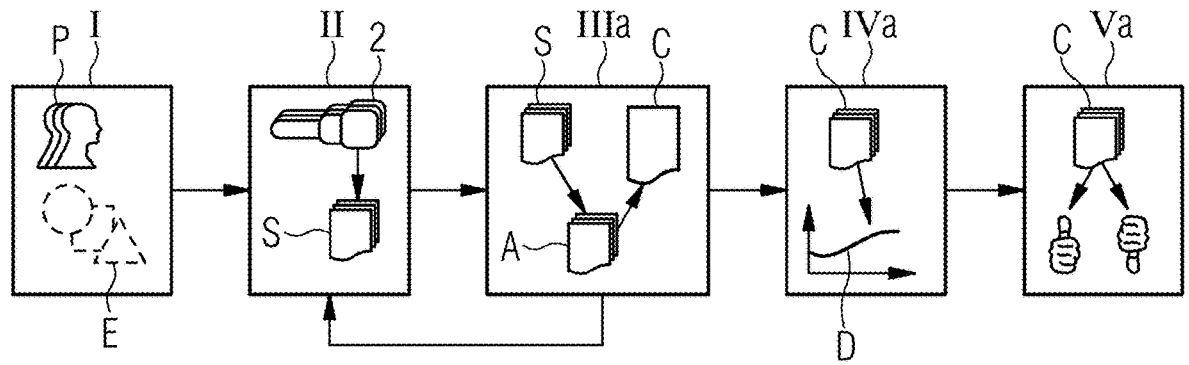
FIG. 3 shows a block diagram for the execution of a preferred method with multiple persons according to one or more example embodiments.

FIG. 3 shows a block diagram for the execution of a preferred method with multiple persons P. The steps are quite similar to FIG. 2, with the difference that here multiple datasets of assessment-data A are generated from multiple sensor-datasets S.

In step IIIa, combined assessment-data C is calculated from the sets of assessment-data A, e.g. an average value.

In step IVa, a progression D of combined assessment-data C is generated from the combined assessment data C over a time period and a trend is observed. Here the trend is rising what may be a good sign or not. In an example, where cognitive load is generated as assessment-data, the rise would indicate to leave the "comfort area" and would be a bad sign.

In step Va, a rating takes place based on the combined assessment-data C, wherein the environment E is rated to be good for the group of persons P or not.

Although the present invention has been disclosed in the form of preferred embodiments and variations thereon, it will be understood that numerous additional modifications and variations could be made thereto without departing from the scope of the invention. For the sake of clarity, it is to be understood that the use of "a" or "an" throughout this application does not exclude a plurality, and "comprising" does not exclude other steps or elements. The expression "a number of" means "at least one". The mention of a "unit" or a "device" does not preclude the use of more than one unit or device. The expression "a number of" has to be understood as "at least one".

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Bluray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

The invention claimed is:

1. A method for monitoring a person in an environment, comprising:
   integrating the person into the environment, wherein the person has a task to solve in the environment;
   measuring with a sensor system a number of physical conditions of the person while the person interacts with the environment, the sensor system providing a sensor-dataset including measured physical values about the person from which mental conditions of the person can be inferred;
   generating assessment-data from the sensor-dataset, the assessment-data reflecting at least one of an ability of the person to accomplish the task or a mental load of the person while solving the task;
   repeating the measuring and the generating a plurality of times;
   outputting the generated assessment-data or data based on the generated assessment-data; and
   adjusting a complexity of the environment based on the generated assessment-data wherein the complexity of the environment is enhanced in response to the generated assessment-data being at least a threshold value and the complexity of the environment is reduced in response to the generated assessment-data being less than the threshold value.

2. The method of claim 1, wherein the environment is an at least partially simulated environment, and at least one sensor of the sensor system is a sensor of a headset used to create a virtual reality or an augmented reality.

3. The method of claim 1, wherein the generated assessment-data comprises a quantitative value of at least one of an attention level of the person, a concentration of the person or an alertness of the person.

4. The method of claim 1, further comprising:
   calculating a trend based on the generated assessment-data generated.

5. The method of claim 1, wherein the generated assessment-data is used for controlling a system biasing the environment.

6. The method of claim 1, wherein data based on the generated assessment-data is control data to control a device that changes aspects of the environment.

7. The method of claim 1, further comprising:
   changing at least one of visual, auditive, olfactory, haptic, somatosensory or gustatory aspects of the environment based on a number of the generated assessment-data, especially.

8. The method of claim 1, wherein
   two or more persons are monitored in the environment by measuring with the sensor system a number of physical conditions of each person while the persons interact with the environment,
   the assessment-data is generated from the sensor-dataset, the generated assessment-data of each person reflecting the ability of the respective person to accomplish the task or the generated assessment-data of a group of persons reflecting the ability of the group to accomplish the task, and
   the generated assessment-data is used for at least one of
      a rating of the environment by comparing the generated assessment-data of the persons with a predefined value and/or classifying load values of the persons and/or comparing the assessment-data of the persons with assessment-data of persons of another environment,
      further developing the environment, or
      assessing or classifying the persons.

9. The method of claim 1, wherein the environment provides a simulation, a learning procedure, a training procedure or a game, wherein a course of a content of the environment is changed depending on the generated assessment-data.

10. A system for monitoring a person in an environment, wherein the system is configured to perform the method of claim 1 and comprises:
    a sensor system configured to measure the physical conditions of the person while interacting with the environment and for providing the sensor-dataset, the sensor-dataset including the measured physical conditions;
    a generation unit configured to generate the assessment-data from the sensor-dataset; and
    an output interface configured to output the generated assessment-data or data based on the generated assessment-data.

11. The system of claim 10, wherein the generation unit is configured to generate at least one of alarm-data, feedback-information, classification data of persons, rating data of the environment or control-data based on the generated assessment-data.

12. The system of claim 10, wherein the generation unit comprises a machine learning model trained on a multitude of sensor-datasets, each sensor-dataset being labeled with detected assessment-data.

13. The system of claim 10, wherein the sensor system comprises at least one of:
    eye tracking sensors, wherein the physical condition includes at least one of an eye movement, an eye opening and closure, an eye status, or pupil properties of the person,
    photoplethysmogram sensors, wherein the physical conditions include at least one of blood volume changes, a heartbeat or breathing,
    at least one of accelerometers or Gyroscopes, wherein the physical conditions include at least one of movements or an inclination,
    electro-encephalograph sensors, wherein the physical conditions include brain activity,
    electromyography sensors, wherein the physical conditions include muscle movements, electrodermal activity sensors, wherein the physical conditions include perspiration,
visual sensors, wherein the physical conditions include at least one of an eye condition, movements of the person or a posture of the person,
temperature sensors, wherein the physical conditions include a body temperature, or
auditory sensors, wherein the physical conditions include a voice of the person.

14. A non-transitory computer program product comprising instructions which, when executed by a computer, cause the computer to perform the measuring and generating of claim 1.

15. A non-transitory computer-readable storage medium comprising instructions which, when executed by a computer, cause the computer to perform the measuring and generating of claim 1.

16. The method of claim 3, wherein the generated assessment-data reflects a quantization of at least one of
emotions,
a change of emotions,
a relation of the person to an actual task,
the person being mentally capable of doing the actual task,
the person being physically capable of doing the task or knowing how to do the task,
how the person experiences the task,
a physical discomfort of the person,
an immersion and presence in a virtual reality or an augmented reality,
an intelligence of the person, or
implicit motives.

17. The method of claim 4, further comprising:
adapting a classification of discrete levels of the generated assessment-data to the person based on a minimum of the generated assessment-data, a maximum of the generated assessment-data and an average of the generated assessment-data.

18. The method of claim 5, further comprising at least one of:
outputting by the sensor system a warning in response to a cognitive load value being outside a predefined range, the cognitive load value being included in the generated assessment-data, or
at least one of providing by the sensor system at least one of learning content and a complexity of the learning content or controlling additional information based on the assessment-data.

19. The method of claim 17, wherein data based on the generated assessment-data is control data to control a device that changes aspects of the environment.

20. The method of claim 19, wherein the environment provides a simulation, a learning procedure, a training procedure or a game, wherein a course of a content of the environment is changed depending on the generated assessment-data.

* * * * *